(12) United States Patent
Lederman

(10) Patent No.: US 9,283,173 B2
(45) Date of Patent: Mar. 15, 2016

(54) EMULSIFIED WAX COMPOSITIONS AND USES THEREOF

(75) Inventor: Uzi Lederman, Hod Hasharon (IL)

(73) Assignee: M.D. LEDERMAN CONSULTING LTD., Hod Hasharon (IL)

( * ) Notice: Subject to any disclaimer, the term of this patent is extended or adjusted under 35 U.S.C. 154(b) by 1011 days.

(21) Appl. No.: 12/811,807

(22) PCT Filed: Jan. 8, 2009

(86) PCT No.: PCT/IL2009/000035
§ 371 (c)(1),
(2), (4) Date: Aug. 3, 2010

(87) PCT Pub. No.: WO2009/087632
PCT Pub. Date: Jul. 16, 2009

(65) Prior Publication Data
US 2010/0297273 A1    Nov. 25, 2010

Related U.S. Application Data

(60) Provisional application No. 61/006,347, filed on Jan. 8, 2008.

(51) Int. Cl.
| A61K 47/44 | (2006.01) |
| A61K 9/00 | (2006.01) |
| A01N 3/00 | (2006.01) |
| A01N 27/00 | (2006.01) |
| A01N 61/00 | (2006.01) |
| A01N 65/00 | (2009.01) |
| A23B 7/16 | (2006.01) |
| A61K 8/06 | (2006.01) |
| A61K 8/36 | (2006.01) |
| A61K 8/44 | (2006.01) |
| A61K 47/02 | (2006.01) |
| A61K 47/10 | (2006.01) |
| A61K 47/12 | (2006.01) |
| A61K 47/18 | (2006.01) |
| A61K 47/26 | (2006.01) |
| A61K 47/34 | (2006.01) |
| A61Q 17/00 | (2006.01) |
| A01N 65/40 | (2009.01) |

(52) U.S. Cl.
CPC .............. *A61K 9/0014* (2013.01); *A01N 3/00* (2013.01); *A01N 27/00* (2013.01); *A01N 61/00* (2013.01); *A01N 65/00* (2013.01); *A01N 65/40* (2013.01); *A23B 7/16* (2013.01); *A61K 8/06* (2013.01); *A61K 8/361* (2013.01); *A61K 8/44* (2013.01); *A61K 9/0034* (2013.01); *A61K 47/02* (2013.01); *A61K 47/10* (2013.01); *A61K 47/12* (2013.01); *A61K 47/183* (2013.01); *A61K 47/26* (2013.01); *A61K 47/34* (2013.01); *A61K 47/44* (2013.01); *A61Q 17/00* (2013.01); *A61K 2800/75* (2013.01)

(58) Field of Classification Search
None
See application file for complete search history.

(56) References Cited

U.S. PATENT DOCUMENTS

| 4,355,046 A | 10/1982 | Suess |
| 4,400,295 A | 8/1983 | Ootsu |
| 4,507,279 A | 3/1985 | Okuyama |
| 4,640,943 A | 2/1987 | Meguro |
| 4,880,627 A | 11/1989 | Trenzeluk |
| 5,688,527 A | 11/1997 | Bordier |
| 6,264,965 B1 | 7/2001 | Roulier |
| 6,375,942 B1 | 4/2002 | Rico |
| 6,419,936 B1 | 7/2002 | Schmoyer |
| 2004/0146617 A1* | 7/2004 | Schrader |
| 2004/0156877 A1 | 8/2004 | Tokuyama |
| 2006/0134043 A1 | 6/2006 | Nakamura |
| 2008/0124292 A1 | 5/2008 | Collin |

FOREIGN PATENT DOCUMENTS

EP    0589047    3/1994

OTHER PUBLICATIONS http://en.wikipedia.org/wiki/Methylchloroisothiazolinone.
Wikepedia_Methylchloroisothiazolinone. Downloaded Sep. 18, 2013.*
Schiltz, John et al., "Retinoic acid induces cyclic changes in epidermal thickness and dermal collagen and glycosaminoglycan biosynthesis rates", J Invest Dermatol, 87(5):663-7 (1986).

* cited by examiner

*Primary Examiner* — Susan Hoffman
(74) *Attorney, Agent, or Firm* — JMB Davis Ben-David

(57) ABSTRACT

The present invention discloses emulsified wax compositions having a wide range of uses, including as cosmetic, pharmaceutical and agricultural compositions, particularly for improving skin moisture, appearance, and wound healing, for the treatment of inflammation and allergic responses of the skin, and for preservation of agricultural fresh produce. The composition of the invention comprises an aqueous phase and at least one wax at a concentration of at least 5%, at least one fatty acid and at least one basic amino acid or a salt thereof.

21 Claims, 2 Drawing Sheets

EMULSIFIED WAX COMPOSITIONS AND USES THEREOF

RELATED APPLICATION DATA

This application is the U.S. national stage of PCT/IL2009/000035, filed Jan. 8, 2009, which claims the benefit of U.S. Provisional Application No. 61/006,347, filed Jan. 8, 2008, the contents of each of which are herein incorporated by reference for all purposes.

FIELD OF THE INVENTION

The present invention relates to emulsified wax compositions having a wide range of uses, including as cosmetic, pharmaceutical and agricultural compositions. The compositions are particularly useful for improving skin moisture, appearance, and wound healing, for the treatment of inflammation and allergic responses of the skin, and for preservation of agricultural fresh produce.

BACKGROUND OF THE INVENTION

Waxes are widely used in the cosmetic, pharmaceutical and agricultural industries. Typically, waxes are formulated in the form of creams and ointments in the form of emulsions, intended for caring for human skin and for topical application of pharmaceutical and cosmeceutical active ingredients. In agriculture, the wax emulsions are used to protect fresh produce, particularly fruit, from cracking, water loss and oxidation.

A wax is generally any of various heat sensitive substances consisting of hydrocarbons or esters of fatty acids that are insoluble in water and soluble in non-polar organic solvents.

Waxes from various sources may be used, among them beeswax and carnauba wax are the most common types in the cosmetic industry. Carnauba is a wax derived from the leaves of a plant native to northeastern Brazil, the Carnauba Palm (*Copernica prunifera*). The wax is secreted by the leaves, apparently in defense against the hot and dry environment of the tree native habitat. The resultant coating is removed by drying and flailing the leaves to loosen the wax, which is then refined and bleached. Carnauba wax contains mainly esters of fatty acids (80-85%), fatty alcohols (10-16%), acids (3-6%) and hydrocarbons (1-3%). Specific for carnauba wax is the content of esterified fatty diols (about 20%), hydroxylated fatty acids (about 6%) and cinnamic acid (about 10%). Cinnamic acid, an antioxidant, may be hydroxylated or methoxylated.

Carnauba wax can produce a glossy finish and as such is used in automobile waxes, shoe polishes, instrument polishes, and floor and furniture polishes, especially when mixed with beeswax. Use for paper coatings is the most common application in the United States.

Because of its hypoallergenic and emollient properties as well as its shine, carnauba wax appears as an ingredient in many cosmetics formulas, particularly to thicken lipstick, eyeliner, mascara, foundation and the like.

As a glazing agent in foods, it finds use particularly in shiny-shelled candies. It is also used in the pharmaceutical industry as a tablet coating agent.

However, it is difficult to incorporate a high percentage of waxes into emulsion compositions since waxes have a tendency to thicken the emulsions considerably. In addition, when a high percentage of wax is incorporated into an emulsion, the emulsion is very difficult to apply to the skin. Moreover, a coarse effect appears on the skin. Such an emulsion is therefore unacceptable to users.

Carnauba wax is among the hardest of natural waxes, being harder than concrete in its pure form. It is practically insoluble in water and ethyl alcohol, and soluble in ethyl acetate and in xylene only on heating. Accordingly, incorporating the carnauba wax into emulsions to enable utilizing its beneficial effects requires even more sophisticated methods and formulations.

Various kinds of wax-containing emulsions and emulsifying agents have been proposed, many targeted to specific cosmetic applications. For example, U.S. Pat. No. 4,507,279 discloses cosmetic composition of the oil-in-water type comprising an oily substance having no free carboxyl group including, inter alia, beeswax and carnauba wax, water, and an emulsifier composed of either a combination of a basic polypeptide and a higher fatty acid or a salt (soap) formed from these compounds.

U.S. Pat. No. 6,264,965 discloses a creamy composition in the form of an oil-in-water emulsion comprising an oily phase dispersed in an aqueous phase, characterized in that it contains at least one anionic emulsifier which is liquid at room temperature, and at least 5% by weight of one or more waxes relative to the total weight of the composition, and in that the oily phase is in the form of a soft paste at room temperature. The anionic emulsifier is preferably a surfactant containing a phosphate group, such as octyldecyl phosphate. A process for preparing this composition, characterized in that at least one step of the process is carried out using a mixer-extruder and uses of the composition in cosmetics and dermatology is also disclosed.

Compact powders for use in cosmetic, pharmaceutical, or food compositions are typically anhydrous compositions which may mainly be composed of solid particles and of a fatty binder, shaped by compression. Use of derivatives of basic amino acids, including lysine, have been proposed for modifying the surface of inorganic substance present in such compositions and for increasing the dispersibility of the compositions (e.g. U.S. Pat. Nos. 4,640,943; 5,688,527; 5,688,527).

U.S. Application Publication No. 2008/0124292, published after the priority date of the present application, discloses compositions useful for coating the eyelashes that address the problem of homogenous dispersion of pigments and waxes in mascara compositions. The compositions of that application contain an aqueous phase and an emulsifying system that comprises at least one specific amino acid compound, including basic amino acids, glutamic acid, sarcosine and glycine.

Individuals typically suffer from various skin ailments that may result from environmental factors, age, wounding, and exposure to chemicals as well as from inflammatory and allergic responses of the skin.

Many attempts have been made to treat these skin conditions. A multi-billion dollar industry comprising hundreds of companies world-wide, produce and supply thousands of different types of creams, salves, balms, ointments and medicaments for healing the skin.

The following are several examples of ointments intended for treatment of the skin. U.S. Pat. No. 4,355,046 discloses a treatment method that moisturizes the skin with a cream containing specially formulated petrolatum, a siloxane solvent, and a microcrystalline wax. U.S. Pat. No. 4,880,627 discloses a skin treatment mixture, comprising a combination of natural ingredient—an extract of the Eupatorium plant, with the chemical ingredients sulfathiazole, petrolatum and zinc oxide.

U.S. Pat. No. 6,375,942 discloses a skin healing ointment comprising a base containing petrolatum, beeswax or other wax, and antibiotic ingredient. These basic ingredients can be combined with zinc oxide and an anti-itch ingredient for universal applicability to, and effective treatment of, various skin disorders.

Some of the attempts were directed to the use of stimulants or certain inhibitors. As an example, collagen stimulation was used for skin treatment (Schiltz, John, et al., J Invest Dermatol 87:663-667).

U.S. Pat. No. 6,419,936 related to a topical skin ointment for application onto the skin of individuals suffering from minor skin irritations such as dry chapped skin, minor cuts, scrapes, and abrasions. The topical skin ointment includes ingredients intended to reduce the discomfort associated with these types of skin irritations as well ingredients intended to promote the natural healing process including vitamins and zinc oxide.

After harvest, vegetables and fruit have a limited shelf-life before deterioration affects their palatability, nutritional value, odor, and aesthetic appearance. Many causes have been identified as attributing to deterioration, including natural enzyme activity, environmental conditions and changes, such as in temperature, moisture and air quality, and contamination by microorganism, insects and other pests. The need to transport the fresh produce from the field to customers, often over considerable distance further contributes to deterioration of the fresh produce quality.

In resemblance to the protection against environmental hazards provided by the mammalian skin, fruit and vegetables also typically comprise a protective outer layer Traditional remedies that have been used to prolong the shelf-life of fruits and vegetables, applied to the outer layer, include chemical bleach washes, alkaline-based washes, and treatment regimes using other chemicals such as sodium ortho phenyl phenate (SOPP), imazalil, and thiabendazole (TBZ). Each of these chemicals is corrosive and may pose underlying human health hazards. Some of these remedies have been discredited as largely ineffective and unnecessarily costly and time consuming. Further, educated consumers often are knowledgeable of the adverse consequences associated with these chemicals and will decline to purchase produce treated with these chemicals.

Thus, there is an unmet need for, and it would be highly advantageous to have, a composition comprising essentially natural elements with high wax concentrations, combining all the features of being easily applicable to a surface, compatible with skin as well as with food products, having protective effects against various environmental hazards and efficient in the treatment of skin conditions and disorders.

SUMMARY OF THE INVENTION

The present invention relates to compositions comprising essentially natural ingredients with high wax concentrations which are highly homogenous and spreadable. The compositions of the present invention have multiple beneficial activities on skin conditions, and thus may be used in cosmetics and as cosmeceuticals and pharmaceutical compositions. Their unique characteristics make them also suitable for agricultural use, particularly for coating agricultural plant fresh produce.

The compositions of the present invention are based on a mixture of an aqueous phase and naturally occurring wax, fatty acids and basic amino acids, which generate a spreadable, membrane-like matrix, which preserves its humidity and elasticity for a long period of time.

The present invention is based in part on the unexpected discovery that combining natural wax at a concentration of at least 5%, including hard waxes such as carnauba wax, with at least one fatty acid and at least one basic amino acid with an aqueous phase provides homogenous and spreadable composition. Furthermore, the present invention now discloses that the composition per se is highly useful in improving skin moisture, appearance, and wound healing and in treating skin conditions and disorders, including, for example, skin itching, inflammation, irritations, burns and the like.

Without wishing to be bound by any particular theory or mechanism of action this skin condition relieving and/or healing may be attributed to the ability of the composition to create at least transiently a special membrane-like or film-like matrix at the treated area. This matrix keeps its own humidity as well as the skin humidity for a long period of time. The composition applied at the treated skin area may not only cover the epidermis but also penetrate and fill the layer between the epidermis and dermis. The concentration ratio of the composition ingredients determines the penetration level and the thickness of the protective layer created. The membrane-like matrix, thus, enables the transport of beneficial agents across the skin without disturbing the natural osmotic balance in the treated area, enhancing the therapeutic effect of the composition. The ability of the matrix to keep the osmotic balance in the treated area while providing continues coating makes it particularly useful for protecting plant fresh produce, particularly fruit and vegetables, from environmental hazards. Moreover, the present invention now discloses that the composition have anti-oxidative activity, further contributing to its preservation efficacy.

Thus, according to one aspect, the present invention provides a composition comprising an aqueous phase and at least one wax at a concentration of at least 5%, at least one fatty acid and at least one basic amino acid or a salt thereof, for administration to a surface.

According to certain embodiments, the composition comprises the at least one fatty acid, at least one wax and at least one basic amino acid at the following ratios: a ratio of at least 1:3 of the at least one fatty acid to wax, and a ratio of at least 4:1 of the combined total amount of said at least one fatty acid and wax to the basic amino acid.

The viscosity of the composition may vary in a wide range of from about 5 to 100,000 centipoise (cps), depending on the intended use. The viscosity of compositions for topical application to a mammal skin is in the range of from 1,000 to 100,000 cps at a temperature of about 20° C. More fluid compositions are used for application to plant fresh produce, in the range of from about 5 to about 1,000 cps. Compositions with higher viscosities are used to form stick-like compositions, e.g. for use as insect repellent or big balm.

According to certain embodiments, the surface is a mammalian skin. According to one embodiment, the mammal is human. According to other embodiments, the surface is of a plant fresh produce, particularly vegetables and fruit.

Any one of essentially natural non-toxic waxes compatible with the skin and/or having food grade can be used in the compositions of the present invention. According to certain embodiments, the wax is selected from the group consisting of carnauba wax, beeswax, candelilla wax rice bran wax and combinations thereof. According to certain currently preferred embodiments, the wax in carnauba wax.

The present invention now discloses that combining at least one wax with at least one fatty acid and at least one basic amino acid with an aqueous phase enables the production of a composition having high wax concentrations, going up to 40%, without negatively affecting the homogenous dispersion of the wax within said composition.

According to certain embodiments, the compositions of the present invention comprise wax at a concentration range of from about 5% to about 40% by weight, with respect to the total weight of the composition. According to typical embodiments, the wax concentration is from about 7% to about 30%, more typically from about 5% to about 15%.

The at least one fatty acid may be saturated or unsaturated. According to certain embodiments, the fatty acid is saturated fatty acids selected from the group consisting of lauric acid, myristic acid, stearic acid, palmitic acid, arachidic acid, behenic acid and derivatives thereof. According to other embodiments the fatty acid is an unsaturated fatty acids selected from the group consisting of palmitoleic acid, oleic acid, linoleic acid and derivatives thereof. According to certain embodiments, the composition comprises $C_8$-$C_{18}$ fatty acids, particularly $C_{12}$-$C_{18}$ fatty acids. According to typical embodiments, the composition comprises a combination of fatty acids. According to other typical embodiments, the composition comprises lauric acid, myristic acid, oleic acid and stearic acid.

According to certain embodiments, the content of the fatty acid(s) ranges from 0.5 to 30% by weight with respect to the total weight of the composition. According to typical embodiments, the content of the fatty acids ranges from 1% to 25%, more typically from 1% to 10%.

The basic amino acids that can be used according to the teachings of the present invention are lysine, arginine, histidine, and derivatives thereof. According to certain currently preferred embodiments, the basic amino acid is lysine.

The content of the at least one basic amino acid in the compositions of the present invention ranges from 0.5% to 15% by weight with respect to the total weight of the composition. According to typical embodiments, the content of the basic amino acid ranges from 1% to 10%, more typically from 1% to 6%.

According to typical embodiments, the composition of the present invention comprises an aqueous phase and carnauba wax at a concentration of at least 5% (based on the total weight of the composition), at least one fatty acid at a concentration of at least 0.5% and at least one basic amino acid at a concentration of at least 0.5%. According to other typical embodiments, the compositions of the present invention comprises an aqueous phase and carnauba wax at a concentration in the range of 7%-30%, a combination of oleic acid, lauric acid, stearic acid and myristic acid at a total combined concentration in the range of 1%-4% and lysine at a concentration in the range of 1%-6%.

According to other embodiments, the composition further comprises at least one surfactant. According to one embodiment, the surfactant is selected from the group consisting of diglycerin, glycerin, glycerol, glycerol polymers, glycol, glycol stearate, glycol stearate SE, carboxylic acid, propylene glycol, avocado (*Persea gratissima*) oil, honey, glyceryl distearate, glyceryl hydroxystearate, glyceryl laurate, glyceryl linoleate, glyceryl myristate, glyceryl oleate, glyceryl stearate, palmitic acid, paraffin, propylene glycol, propylene glycol dipelargonate, propylene glycol laurate, propylene glycol stearate, propylene glycol stearate SE and stearoxy.

Additional ingredients may be added to the compositions of the present invention, for improving its appearance, texture or activity.

According to certain embodiments, the composition further comprises at least one complex sugar; said at least one complex sugar may be selected from the group consisting of fructose, glucose, sucrose, sucrose fatty acid ester, sucrose acetate isobutyrate (SAIB), and sorbitol.

According to further embodiments, the composition further comprises at least one preservative. Any preservative useful in the cosmetic or food industry as is known to a person skilled in the art may be used with the compositions of the present invention. According to certain embodiments, the preservative is selected from the group consisting of propylparaben, methylparaben, phenoxyethanol, methylisothiazolinone, methylchloroisothiazolinone and other parabens.

According to certain embodiments, the composition further comprises at least one viscosity agent. According to one embodiment, the viscosity agent is selected from the group consisting of sodium polyacrylate, ethylhexyl stearate and trideceth-6.

According to other embodiments, the composition further comprises KOH (potassium hydroxide).

According to certain embodiments, the pH of the composition is in the range of 6.0-9.5. According to typical embodiment, the pH of a composition for cosmetic or cosmeceutical use is in the range of 6.5-8.5 According to other typical embodiments, the composition for agricultural composition is in a pH range of 7.0-9.5.

To enhance the spreadability of the matrix of the present invention, additional film-forming biopolymers may bee added. According to certain embodiments, the film-forming polymer is hyaluronic acid. According to certain embodiments, the concentration of the hyaluronic acid is from about 0.1%-10%, particularly 0.5%-2.0% by weight with respect to the total weight of the composition.

According to typical embodiments, the composition of the present invention directed to topical application to a mammal skin comprises the following mixture of ingredients: wax at about 5%-30% of said mixture; fatty acids at about 1%-2%; lysine HCl at about 1%-6%; sorbitol at approximately 0.1-10%; glycerin at about 0.8-7%; potassium hydroxide at about 0.05%-0.5%; peppermint oil at about 0.001-1%; perfume at about 0.001-1%; preservatives at about 0.001-2%; sucrose fatty acid ester at about 0.001-10% and sucrose Acetate isobutyrate at about 0.001-10%; demineralized water at about 20.5% to about 92%, wherein the wax is selected from the group consisting of bee wax and carnauba wax, particularly carnauba wax; the fatty acids are selected from the group consisting of lauric acid, myristic acid, stearic acid, oleic acid, and palmitic acid and combinations thereof; and the preservatives are selected from the group consisting of propylparaben, methylparaben, phenoxyethanol, methylisothiazolinone, methylchloroisothiazolinone and other parabens.

The compositions of the present invention may appear in the form of emulsion or dispersion, depending on the method of production. As used herein, a composition in the form of emulsion comprises particles of a size smaller than 1 micron. A composition in the form of dispersion comprises particles having a size above 1 micron.

According to certain embodiments, the compositions of the present invention are useful for cosmetic applications. According to other embodiments, the compositions are used as cosmeceuticals. According to further embodiments, the compositions are useful for therapeutic use. According to yet further embodiments the compositions are used in agriculture, particularly for coating plant fresh produce as to prolong their shelf life.

According to another aspect, the present invention provides a method of treating skin conditions and disorders comprising topically applying to the skin a therapeutically effective amount of a composition of the present invention.

Surprisingly, the present invention now shows that the compositions of the present invention are effective in treating a wide range of skin ailments, including psoriasis and herpes. Moreover, a relief of the symptoms at the treated area is typically detected short time (at the range of minutes to hours) after the composition is applied. It is to be explicitly understood that relief of the symptoms includes relief of the pain associated with the various skin conditions and disorders.

According to certain embodiments, the skin condition or disorder is selected from the group consisting of skin irritation, skin itching, pruritus, sore skin, redness, burns and wounds. According to certain embodiments, the skin disorder is a result of a disease, including psoriasis and herpes. According to other embodiments, skin itching or irritation is the result of mosquito bite or jellyfish sting. According to further embodiments, the itching or irritation is the result of contact with chemicals, including insect repellent, and with natural irritants and rashes including, e.g. poison ivy, oak and Stinging Nettle. According to yet further embodiments, the skin disorder is the result of diabetes, including diabetes sores, wounds and other skin ailments resulting from diabetes.

According to additional aspect, the compositions of the present invention are used as insect repellent, particularly lice and mosquito.

The administration regime and the mode of application of the compositions of the present invention will depend on parameters associated with the phenomena to be treated as well as on characteristics of the treated individual (age, size, gender, etc.). Typically, best results will be obtained by applying the composition to the affected skin as soon as possible, particularly when the skin is burned or wounded.

According to further aspect, the present invention discloses use of at least one wax, at least one fatty acid, at least one basic amino acid or a salt thereof and an aqueous phase for the preparation of a medicament useful in treating skin conditions and disorders.

According to additional aspect, the present invention provides a method for preserving agricultural plant fresh produce, comprising administering to the surface of the fresh produce an agriculturally effective amount of a composition of the present invention, so as to preserve the characteristics of said fresh produce at the day of picking for at least 15 days.

According to certain embodiments, the plant fresh produce is selected from fruit and vegetables.

According to certain embodiments, the composition is administered to the surface of the fresh produce by immersion or spraying. According to other embodiments, administration is performed in a time range of from right after picking to 24 h after picking, typically from 1 h to 12 h after picking, more typically from 4-17 h after picking.

Other objects, features and advantages of the present invention will become clear from the following description and drawings.

DETAILED DESCRIPTION OF THE INVENTION

Figure 1:
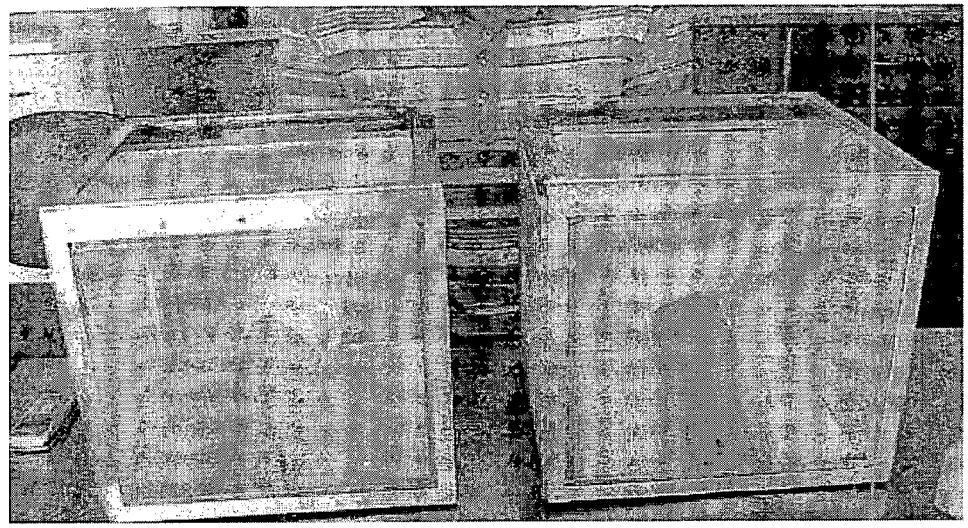
FIG. 1 shows the apparatus for examining the mosquito repellent activity of the composition of the invention.

The present invention provides compositions comprising essentially natural ingredient, said compositions comprising high concentration of homogenously dispersed natural waxes, particularly carnauba wax. The homogeneity and viscosity of the compositions make them highly suitable for topical application to the mammal skin, as well as for application to the surface of agricultural fresh produce. Unexpectedly, the present invention now shows that the particular combination of the composition ingredient, including natural wax(s), fatty acid(s) and basic amino acid(s) not only provide for the advantageous physical characteristics of the composition but also to its efficacy in treating and/or relieving skin conditions and disorders as well as in preserving agricultural fresh produce.

DEFINITIONS

The term "wax" as used herein refers to a lipophilic compound which is solid at ambient temperature (25° C.), which exhibits a reversible solid/liquid change in state and which has a melting point of greater than or equal to 30° C. that can range up to 120° C. The melting point of the wax can be measured using a differential scanning calorimeter (DSC). The waxes according to the present invention are esters of fatty acids with long chain monohydric alcohols (one hydroxyl group). Natural waxes are often mixtures of such esters, and may also contain hydrocarbons as in, e.g. carnauba wax. Waxes are widely distributed in nature. The leaves and fruits of many plants have waxy coatings, which may protect them from dehydration and small predators. The feathers of birds and the fur of some animals have similar coatings which serve as a water repellent. Specifically, carnauba wax is valued for its toughness and water resistance.

As used in the context of the present invention the term "basic amino acid" refers to the amino acids lysine, arginine and histidine, having a basic side-chain. As used herein, the term "lysine" shall mean, the lysine amino acid which is typically abbreviated as Lys or K. Lysine is an essential amino acid, which cannot be synthesized by humans. The term lysine shall also encompass any lysine which has been modified by esterification, or other acid-base reactions, reduction, oxidation, hydrogenation, acetylation, hydroxylation, methylation, ubiquitylation, sumoylation and other modifications known in the art.

It should be appreciated that the lysine of the present invention also includes lysine salts, lysine derivatives, and intermediates. The term lysine of the present invention may encompass lysine products which comprise lysine, such as but not limited to Lysine HCl (hydrochloride). The term lysine shall include both L-lysine and D-lysine configurations.

As used herein, the term "arginine" refers to the arginine amino acid which is typically abbreviated as Arg or R. The term arginine shall also encompass any arginine which has been modified by esterification, or other acid-base reactions, reduction, oxidation, hydrogenation, acetylation, hydroxylation, methylation, ubiquitylation, sumoylation and other modifications known in the art.

It should be appreciated that the Arginine of the present invention also includes arginine salts, arginine derivatives, and intermediates. The term arginine of the present invention may encompass arginine products which comprise arginine, such as but not limited to arginine HCl (hydrochloride). The term arginine shall include both L-arginine and D-arginine configurations.

As used herein, term "histidine" refers to the histidine amino acid which is typically abbreviated as His or H. The term histidine shall also encompass any histidine which has been modified by esterification, or other acid-base reactions, reduction, oxidation, hydrogenation, acetylation, hydroxylation, methylation, ubiquitylation, sumoylation and other modifications known in the art.

It should be appreciated that the histidine of the present invention also includes histidine salts, and histidine derivatives. The term histidine of the present invention may encompass histidine products which comprise histidine, such as but not limited to histidine HCl (hydrochloride). The term histidine shall include both L-histidine and D-histidine configurations.

The term "fatty acid" as used herein refers to a carboxylic acid often with a long aliphatic tail or a hydrocarbon chain. Fatty acids of the present invention can either be saturated or unsaturated. The unsaturated fatty acids of the present invention may be either cis or trans fatty acids, and also may comprise functional group(s) along the chain. According to certain embodiments the fatty acids of the present invention may comprise carboxylic acids of from 4 to 30 carbon atoms, such as but not limited to 10-18 carbon atoms. The fatty acids of the present invention may be natural or synthetic fatty acids. In that respect, synthetic fatty acid encompasses any fatty acid synthesis process known in the art. The fatty acids can have an even number of carbon atoms, but also an odd number of carbon atoms. The fatty acids of the present invention can be monounsaturated fatty acids, or polyunsaturated fatty acids. The fatty acids of the present invention also include any fatty acid which has been modified by chain elongation, desaturation, or other modifying process known in the art. The fatty acids of the present invention also encompass any fatty acid which like any other carboxylic acid has been modified by esterification, or other acid-base reactions, reduction, oxidation, auto-oxidation, or hydrogenation. It should be appreciated that the fatty acids of the present invention also include fatty acids derivatives, intermediates, and fatty alcohols.

The term "derivative" shall mean a compound produced from or related to another.

The term "percent" and the symbol "%" shall mean throughout the application percent by weight. In certain embodiment, the term refers to percent by weight with respect to the total weight of the composition.

For the purposes of the present invention, the term "skin conditions" shall mean wounded skin, including open wounds, freshly damaged skin, wet wounds, unhealed xerotic eczema, unhealed cicatricial skin lesions, dried skin, skin inflicted with inflammation of any type, herpes sores, allergic responses of the skin, irritant appearance, pressure sores, diabetes sores and other diabetes associated skin ailments, acne, mosquito bites, jellyfish stings, skin burns, sun burn, red appearance, purulence, deep wrinkles, black eye circles, and other skin ailments.

As used herein, the term "characteristics of a plant fresh produce" refers to the characteristics commonly used in the field of agricultural storage and transport with regard to a particular plant species, including, but not limited to weight, color, smell, presence of microorganism, ripening stage, taste and the like.

PREFERRED MODES FOR CARRYING OUT THE INVENTION

According to one aspect, the present invention provides a composition comprising an aqueous phase and at least one wax at a concentration of at least 5%, at least one fatty acid and at least one basic amino acid or a salt thereof, for administration to a surface.

According to certain embodiments, the ratio of the at least one fatty acid to wax is at least 1:3 and the ratio of the combined total amount of said at least one fatty acid and wax to the at least one basic amino acid is at least 4:1.

Wax is essential component in the composition of the present invention, and can be any one of non-toxic, cosmetic and/or food grade waxes as are known to a person skilled in the art. According to certain embodiments, the wax is hydrocarbon wax, selected from the group consisting of beeswax, lanolin wax and Chinese insect waxes; rice wax, carnauba wax, candelilla wax, ouricury wax, esparto wax, cork fibre wax, sugarcane wax, Japan wax and sumac wax; montan wax, microcrystalline waxes, paraffin waxes and ozokerite; polyethylene waxes, waxes obtained by the Fischer-Tropsch synthesis and waxy copolymers, and also their esters. In particular embodiments, the compositions of the present invention comprise carnauba wax. The wax concentration ranges from about 5% to about 40% (w/w), typically at least 7% in therapeutically effective compositions for treating mammalian skin, and at least 15% in agricultural compositions for preserving plant fresh produce.

The wax or waxes can be present in the form of an aqueous wax dispersion or emulsion. The term "aqueous wax dispersion" is understood to mean an aqueous dispersion of wax particles in which the size of the wax particles is equal or more than approximately 1µ. The term "aqueous wax emulsion" is understood to mean an aqueous emulsion of wax particles in which the size of the wax particles is less than 1µ. In both forms the colloidal wax particles are stably dispersed in the composition.

Another essential component of the composition of the present invention is at least one fatty acid. According to certain embodiments, the fatty acid is $C_8$-$C_{18}$ fatty acids, particularly $C_{12}$-$C_{18}$ fatty acids.

The $C_8$-$C_{18}$ fatty acid or acids which can be used in the compositions according to the present application is/are preferably chosen from saturated or unsaturated fatty acids comprising from 8 to 18 carbon atoms and their mixtures.

Some specific examples of fatty acids that may be used in accordance with the present invention are listed below:

| Formula | Common name |
|---|---|
| Saturated fatty acids | |
| $CH_3(CH_2)_{10}CO_2H$ | Lauric acid |
| $CH_3(CH_2)_{12}CO_2H$ | Myristic acid |
| $CH_3(CH_2)_{14}CO_2H$ | Palmitic acid |
| $CH_3(CH_2)_{16}CO_2H$ | Stearic acid |
| $CH_3(CH_2)_{18}CO_2H$ | Arachidic acid |
| Unsaturated fatty acid | |
| $CH_3(CH_2)_5CH=CH(CH_2)_7CO_2H$ | Palmitoleic acid |
| $CH_3(CH_2)_7CH=CH(CH_2)_7CO_2H$ | Oleic acid |
| $CH_3(CH_2)_4CH=CHCH_2CH=CH(CH_2)_7CO_2H$ | Linoleic acid |

According to certain embodiments, the fatty acids in accordance with the present invention are selected from the group consisting of the saturated fatty acids lauric acid, myristic acid, stearic acid, palmitic acid, arachidic acid and derivatives thereof, and the unsaturated fatty acids palmitoleic acid, oleic acid, linoleic acid and derivatives thereof. Moreover, the present invention also pertains to combinations of fatty acids being selected from said group in any concentration as defined herein. According to other typical embodiments, the composition comprises lauric acid, myristic acid, oleic acid and stearic acid.

According to certain embodiments, the content of the fatty acid(s) ranges from 0.5 to 30% by weight with respect to the total weight of the composition. According to typical embodiments, the content of the fatty acids ranges from 1% to 25%, more typically from 1% to 10%.

The wax containing compositions of the invention can be obtained by melting the wax in the presence of fatty acids and optionally of a portion of the water and then gradually adding hot water with stirring. The intermediate formation of an emulsion of the water-in-oil type, followed by phase inversion, with an emulsion or dispersion of oil-in-water type finally being obtained, is observed. On cooling, an emulsion or dispersion of solid colloidal wax particles is obtained.

As used herein, the term oil-in-water (O/W) emulsion refers to an emulsion consisting of droplets of oil dispersed in water, and the term water-in-oil (W/O) refers to an emulsion in which the phases are reversed, i.e. droplet of water dispersed in oil. The continuous liquid is referred to as the dispersion medium, and the liquid which is in the form of droplets is called the disperse phase.

The wax emulsion or dispersion can also be obtained by stirring the mixture of wax, fatty acids and of water using stirring means, such as ultrasound, a high-pressure homogenizer or turbine mixers.

Additional essential component of the compositions of the present invention is at least one basic amino acid. The basic amino acids that can be used according to the teachings of the present invention are lysine, arginine, histidine, and derivatives thereof. According to certain currently preferred embodiments, the basic amino acid is lysine. The basic amino acid is added to the emulsion or dispersion of the solid colloidal wax particles. Without wishing to be bound by particular theory or mechanism of action, the addition of at least one basic amino acid to the wax emulsion/dispersion, particularly lysine, may contribute to the beneficial effects of the compositions of the present invention on skin.

The content of the at least one basic amino acid in the compositions of the present invention ranges from 0.5 to 15% by weight with respect to the total weight of the composition. According to typical embodiments, the content of the basic amino acids ranges from 1% to 10%, more typically from 1% to 6%.

A person of ordinary skill in the art would understand that the concentration of the various essential components of the compositions of the present invention could vary according to the required use and formulation. Typically, while the concentrations are different, the ratio between the components is preserved. According to certain embodiments, the ratio of the at least one fatty acid to wax is at least 1:3 and the ratio of the combined total amount of said at least one fatty acid and wax to the at least one basic amino acid is at least 4:1. The compositions of the present invention can further comprise additional substances useful for the formulation of the composition for the desired use, including as cosmetic, cosmeceutical, pharmaceutical and agricultural composition, as is known to a person skilled in the art.

Wax emulsions or dispersions are typically thick, difficult to apply to a surface and form a rough layer. The present invention now discloses wax-containing compositions having satisfactory fluidity such that the composition can be easily spread on a surface. Moreover, the composition preserves the surface as well as its own humidity. When applied to the skin, the composition has a pleasant sensation.

Additional ingredients may be added to the compositions of the present invention, for improving its appearance, texture or activity. The nature and amount of the additional ingredients will be determined according to the intended use of the composition as cosmetic, pharmaceutical or agricultural composition, as is well known to a person skilled in the art. Thus, the present invention encompasses the compositions of the present invention further comprising cosmetically, pharmaceutically or agriculturally acceptable diluent or carrier.

According to certain embodiments, the composition further comprises at least one surfactant. According to one embodiment, the surfactant is selected from the group consisting of diglycerin, glycerin, glycerol, glycerol polymers, glycol, glycol stearate, glycol stearate SE, carboxylic acid, propylene glycol, avocado (Persea gratissima) oil, honey, glyceryl distearate, glyceryl hydroxystearate, glyceryl laurate, glyceryl linoleate, glyceryl myristate, glyceryl oleate, glyceryl stearate, palmitic acid, paraffin, propylene glycol, propylene glycol dipelargonate, propylene glycol laurate, propylene glycol stearate, propylene glycol stearate SE and stearoxy.

According to certain embodiments, the composition further comprises at least one complex sugar; said at least one complex sugar may be selected from the group consisting of fructose, glucose, sucrose, sucrose fatty acid ester, sucrose acetate isobutyrate (SAIB), and sorbitol.

According to further embodiments, the composition further comprises at least one preservative. Any preservative useful in the cosmetic, pharmaceutics or food industry as is known to a person skilled in the art may be used with the compositions of the present invention. According to certain embodiments, the preservative is selected from the group consisting of propylparaben, methylparaben, phenoxyethanol, methylisothiazolinone, methylchloroisothiazolinone and other parabens.

The viscosity of the compositions of the present invention is determined by the concentration of the essential composition components, the pH and the mode of preparation, particularly the rate in which water is added to the melted wax and fatty acids. The viscosity may be further adjusted by the addition of at least one viscosity agent. According to certain embodiments, the viscosity agent is selected from the group consisting of sodium polyacrylate, ethylhexyl stearate and trideceth-6.

The viscosity of the compositions of the present invention may vary according to the intended use. According to certain embodiments, the viscosity of compositions for topical application to a mammal skin is in the range of from 1,000 to 100,000 cps at a temperature of about 20° C.

More fluid compositions are required for application to plant fresh produce, as application in typically be way of immersion or spraying. According to certain embodiments, the viscosity of compositions for application to plant fresh produce is in the range of from about 5 to about 1,000 cps.

Viscosity values of the compositions of the present invention are as determined with Brookfield Viscometer DVII 20/4 at 20° C.

According to other embodiments, the composition further comprises KOH (potassium hydroxide), which is added as a solution in glycerin to the melted wax and fatty acids.

According to certain embodiments, the compositions of the present invention are devoid of exogenous pigments or dyes. According to other embodiments, the compositions of the present invention are devoid of an amino acid component selected from the group consisting of glutamic acid, sarcosine and glycine.

According to certain embodiments, the pH of the composition is in the range of 6.0-9.5. According to typical embodiment, the pH of a composition for cosmetic or pharmaceutical use is in the range of 6.5-8.5 According to other typical embodiments, the composition for agricultural composition is in a pH range of 7.0-9.5.

To enhance the spreadability of the matrix of the present invention, additional film-forming biopolymers may bee added. According to certain embodiments, the film-forming polymer is hyaluronic acid. According to certain embodiments, the concentration of the hyaluronic acid is from about 0.1%-10%, particularly 0.5%-2.0% by weight with respect to the total weight of the composition.

According to additional embodiments, the compositions of the present invention further comprise at least one active ingredient selected from the group consisting of, but not limited to, an anti-oxidant, an anti-inflammation agent, a vitamin, a carotenoid, a UV absorbing agent a UV protecting agent or any combination thereof.

According to another aspect, the present invention provides a method of treating skin conditions and disorders comprising topically applying to the skin an effective amount of a composition of the present invention.

Surprisingly, the compositions of the present invention have been found to have beneficial activities on a wide range of skin conditions and ailments. For example, as described in details in Example 2 hereinbelow, the composition is highly effective in treating herpes. The composition is also effective in treating skin irritation, skin itching, pruritus, sore skin, redness, burns and wounds resulting from local skin abuse or chronic disease, including psoriasis, diabetes and the like.

Irrespective to the cause of the skin condition, a relief of the symptoms after applying the compositions of the invention is typically observed after a shorter time as compared to application of respective commonly used compositions. Such relief may be observed within a time scale of minutes to hours. However, it is to be understood that the preferable amounts and the administration regimes will depend on parameters associated with the phenomena to be treated as well as on characteristics of the treated individual (age, size, gender, etc.). It is a common practice that a medicament or cosmetic composition should be applied in a regime where few applications per day for a certain period is required; however, a permanent relief of the symptoms is expected after completing the treatment regime.

It should be noted that the above-described division of the compositions for cosmetic or pharmaceutical use is somewhat artificial inasmuch as the activity may be determined by the amount of the composition or the number of successive applications required. In certain situations, the amount and duration of use might be guided by the results obtained during treating.

Examined by Draize Repeated Insult Patch Test (RIPT), the compositions of the present invention were found to be highly tolerated by skin, with no disadvantageous reactions such as irritation or sensitization.

According to additional aspect, the compositions of the present invention are used as insect repellent, particularly lice and mosquito. As exemplified in Example 4 hereinbelow, applying the composition of the invention to a subject hand and exposing the hand to hungry mosquitoes within a cage (FIG. 1), efficiently prevented mosquitoes from landing and biting the exposed treated skin area. Without wishing to be bound by any specific mechanism of action or theory, the composition of the invention has a dual activity of repelling the mosquitoes from landing on the skin and preventing the penetration of the mosquito proboscis into the skin by the formation of a membrane-like matrix at the skin level.

According to additional aspect, the present invention provides a method for preserving agricultural plant fresh produce, comprising administering to the surface of the fresh produce an agriculturally effective amount of a composition of the present invention, so as to preserve the characteristics of said fresh produce at the day of picking for at least 15 days.

According to certain embodiments, the plant fresh produce is selected from fruit and vegetables.

After harvesting, fresh fruit and vegetables are commonly stored for variable periods before being placed on the market for consumption within a few days. It is important for fruit and vegetables not to lose quality, in particular appearance, during the storage period. The fresh produce is susceptible to degradation, in particular by the proliferation of fungi at its surface, leading to rapid deterioration of the affected fruit or vegetable. The visible damage is typically a result of deleterious oxidative processes leading to the accumulation of oxidized products accumulating in the waxy surface coat, and possibly reaching down to the pulp of the fruit (e.g. in the case of apples and pears). These deteriorations are even faster if the fruit or vegetable has any small bruises consisting of nicks in the skin. Various synthetic antioxidant substances have been proposed to overcome this phenomenon, including, for example, diphenylamine; ethoxyquine; 3-tert-butyl-4-hydroxyanisole and 2-tert-butyl-4-hydroxyanisole (BHA); 2,6-di-tert-butyl-p-cresol (BHT); and tert-butylhydroquinone (TBHQ). These compounds are usually applied to the fruit and vegetables at ambient temperature on account of their powerful antioxidant activity. However, they may present a certain level of toxicity to the consumer. The compositions of the present invention overcome this shortage of hitherto known compound, providing a safe, stable and efficient protection of fresh produce from the deleterious effects associated with periods of storage.

According to the invention, the fruit and vegetables can be treated just after harvesting or during the period of conservation and storage. Preferably, this treatment is carried out just after harvesting.

The following examples are presented in order to more fully illustrate some embodiments of the invention. They should, in no way be construed, however, as limiting the broad scope of the invention. One skilled in the art can readily devise many variations and modifications of the principles disclosed herein without departing from the scope of the invention.

EXAMPLES

Example 1

Preparation of the Compositions of the Invention

General Method

In a first step, a mixture comprising carnauba (*Copernicia Cerifera*) wax 5-40% together with oleic acid 0-20%, lauric acid 0-6%, myristic acid 0-30%, stearic acid 0-2% (wherein the combined total concentration of fatty acids is from 0.5% to 30%) were melted at 110° C. in a high speed closed reactor. The pressure in the reactor was set to about 5-20 bar. Potassium hydroxide-solid in glycerin 0.05-3% was added to the mixture of melted wax and fatty acids while stirring. The temperature was raised to approximately 120° C. for about 10-30 minutes. Demineralized water of about 90-120° C. was added to said mixture very slowly while stirring, during a period of about 10-120 min.

At this stage an emulsified wax in the form of a low-viscosity (liquid-like) emulsion was obtained. Following the addition of demineralized water, the temperature was first lowered to about 90-100° C. Thereafter the temperature was further lowered as quickly as possible to below 30° C. Following the cooling phase, a white glossy transparent composition was created.

As a second step, a mixture of demineralized water ranging 0.1-30%, L-lysine HCL ranging 1%-6%, glycerin 0.5%-20%, and sorbitol 0.1%-10% was prepared in a kettle mixing system. The product of step 1 was then added and stirred into the mixture. Without wishing to be bound by any specific mechanism of action or theory, the addition of lysine contributes to the formation of a spreadable composition which preserves its humidity and elasticity.

Step 3 included the preparation of a mixture of demineralized water ranging 0.1%-10%, sucrose acetate isobutyrate 0-10%, sucrose fatty acid ester 0-10%, and liquid fructose ranging 0-10% by stirring and mixing in the kettle. Phenoxyethanol ranging 0-1% and a mixture of N-triethylene glycol, benzyl alcohol, propylene glycol and chloromethylisothiazolinone together ranging 0-1% were added and stirred at about 500-1500 rpm.

In step 4, a mixture of sodium polyacrylate and ethylhexyl stearate and trideceth-6 together ranging 0-6% was added until suitable viscosity of the emulsified wax was exhibited. Suitable viscosity in this respect depends on the particular use of the composition, and may range from 5 cps for liquid-like compositions spread by roller or brush to 100,000 cps for ointments.

The composition so prepared exhibited white/gray color. Importantly, the composition prepared is characterized in water solubility, pH of 6.0-9.0 and viscosity of 5-100,000 cps (depending on the type of use), and no noticeable odor.

Based on the above-described procedure, several compositions, each particularly suitable for a different use, were prepared.

Composition for Topical Application to Mammalian Skin

| Compound | Concentration (%) |
|---|---|
| Stage 1 | |
| Oleic acid | 0-4 |
| Lauric acid | 0-6 |
| Myristic acid | 0-3 |
| Stearic acid | 0-2 |
| Total fatty acids | 1-6 |
| Carnauba wax | 7-30 |
| Bee wax | 0-10 |
| KOH-solid | 0.08-3 |
| Glycerin | 0.8-6 |
| Ammonia | 0-3 |
| Anti-foam | 0-1 |
| Demineralized water | 40-91.2 |
| Stage 2 | |
| Stage 1 | 34-97 |
| Demineralized water | 1-30 |
| L-lysine | 1-6 |
| Glycerin | 1-20 |
| Sorbitol | 0.1-10 |
| Stage 3 | |
| N-triethylene glycol benzyl alcohol propylene glycol chloromethylisothiazolinone | 0.01-1 |
| Phenoxyethanol | 0.01-1 |
| Sucrose acetate isobutyrate | 0.1-10 |
| Sucrose Fatty acid ester | 0.1-10 |
| Liquid fructose | 1-10 |
| Stage 2 | 62-98.68 |
| Sodium polyacrylate Ethyhexyl stearate Trideceth-6 | 0.2-6 | pH of the Composition: 6.5-8.5

Example 2

Treatment of Herpes Simplex

Herpes is a viral disease that primarily infects mucosal tissues and skin, mostly at the tips area and genitals. The virus is transferred through very small cracks in the skin and cannot be transmitted through healthy skin. Following initial infection the virus is chronically present in the host's body in a dormant state. The frequency of outbreaks vary from person to person, typically the virus being expressed when the immune system is weak. The following study was conducted to test the efficacy of the topical composition prepared as described hereinabove in treating patients with Herpes simplex. The study has been performed by The Institute for Skin Research in Tel Aviv, Israel.

Inclusion Criteria:
Volunteers aged 18-65 with Herpes (clinically assessed).
Volunteers signed an informed consent form prior to the test and after a detailed explanation.

Exclusion Criteria:
Volunteers with a known allergy to one of the tested materials, medication or repeated skin diseases.
Volunteers with known sensitivity to external products.
Treatment with medication such as anti-inflammatory medications, anti-histamines and corticosteroids, applied systemically or topically.
Volunteers with scars, lesions or any other factor that can interfere with the study product.
Pregnant or lactating women.
History of sun hypersensitivity, photosensitive dermatoses, or recent sunburn.

Test Performance:
10 volunteers aged 18-65 participated in the trial. The volunteers signed a consent form prior to the test and after a detailed explanation.

The volunteers were instructed to apply the product as follows: first 2 days—six times a day, day 3+4—five times a day, day 5+6—three times a day; total duration of the treatment—6 days.

Each volunteer was examined at baseline ($T_0$), and after one week of using the product ($T_1$). The Study Director rated the state of the skin according to the following skin parameters: blisters, redness, pustules and crusts. Rating was performed according to a predetermined scale, wherein 0=absent; 1=slight; 2=moderate; 3=severe; 4=extreme; and 5=very extreme. The state of the treated area was documented with color photographs at $T_0$ and $T_1$. In addition, each volunteer was asked to answer a questionnaire regarding the tested product and regarding previous outbreaks.

The participants were asked to keep a record of daily applications and to note any side-effect as a result of the product application.

Side Effects:
Volunteers were asked to report any side effects, such as dryness, burning sensation, peeling of the skin, redness, etc. immediately to the Study Director, in addition to keeping a record of all side effects.

Statistical Analysis:

A statistical comparison between $T_0$ and $T_1$ was made according to the Wilcoxon signed-ranks test, where $p<0.05$ indicates a significant difference.

Results

Skin Conditions

Blisters—The total severity rate at the treated area was 2.7 at $T_0$ and decreased to 0.5 at $T_1$. The improvement in the treated skin was found to be significant according to Wilcoxon signed-ranks test ($p<0.05$).

Pustules—As rated by the investigator, the total severity rate at the treated area was 1.1 at $T_0$ and decreased to 0.5 at $T_1$. According to Wilcoxon signed-ranks test, the change of the pustules in the treated area was not found to be significant ($p<0.05$).

Redness—As rated by the investigator, the total severity at the treated area was 2.8 at $T_0$ and decreased to 1.3 at $T_1$. The improvement of redness in the treated skin was found to be significant according to Wilcoxon signed-ranks test ($p<0.05$).

Crusts—As rated by the investigator the total severity rate at the treated area was 0.8 at $T_0$ and increased to 1.2 at $T_1$. According to Wilcoxon signed-ranks test, change of the crusts in the treated area was not found to be significant ($p<0.05$).

Outbreak Evaluation

The patients participating in the study were asked to fill questionnaires regarding past outbreaks in order to compare between past and study outbreaks regarding treatment efficacy.

For one volunteer out of ten, the current outbreak was the first. Therefore, all questions regarding past outbreaks were answered by 9 volunteers only. 67% of the volunteers experienced 1-3 outbreaks in the past, 22% more than 7-9, and 11% 4-6 outbreaks. Sixty percent (60%) of the patients reported the past outbreak duration to be of 7-9 days, 20% reported a duration of 4-6 days, 10% 1-3 days and 10% reported more than 7-9 days. The duration of the study outbreak was either 4-6 days (50% of the patients) or more than 7 days (50% of the patients).

At the end of the study, the volunteers were asked to grade the sensation using a 1-5 scale, wherein 1 is lack of intensity/appearance and 5 is strong sensitivity/appearance of the sensation. Comparison of sensation after treatment with the composition of the invention and treated past outbreaks is given in Table 1 hereinbelow.

TABLE 1

Comparison of sensation parameters between past and study outbreaks

| Sensation Parameter | Past outbreak | Current outbreak |
|---|---|---|
| Pain | 3.00 | 2.60 |
| Burning | 3.44 | 2.70 |
| Local heat | 2.67 | 2.20 |
| Itching | 2.89 | 2.67 |
| Stinging | 3.67 | 2.40 |
| Redness | 4.11 | 3.10 |
| Blisters | 3.11 | 2.00 |
| Scales | 3.89 | 3.00 |

Summary

As a result of using the composition of the present invention a significant decrease was observed in the redness and blister level at the treated area ($p<0.05$). The analysis of the questionnaires showed a clear difference between treatments with various products of past outbreaks and the study treatment. The composition of the invention decreased the sensation parameters of the herpes outbreak noticeably, and at the same time reduced its duration.

Example 3

Determination of the Composition Sensitizing Properties

The composition prepared as described hereinabove has been tested for its sensitizing properties using Draize Repeated Insult Patch Test (RIPT) performed with human volunteers. The study has been performed by The Institute for Skin Research (ISR) in Tel Aviv, Israel. The study was carried out in accordance with the Good Clinical Practice and Standards established by the International Standardization Organization (ISO), and the standard operating procedures of the ISR. The Quality Assurance Auditor testifies to the adherence to the rules, standards and procedures, and to the control of raw and final data emanating from this study.

Method

The method employed in carrying out the test is similar to that described in "Appraisal of the Safety of Chemicals in Foods, Drugs and Cosmetics" by J. H. Draize and published by the Association of Food and Drug Officials of the United States.

Briefly, the sensitizing properties were evaluated by a patch preparation consisting of an occlusive application of the product by Finn Chamber/Hill Top Chamber/Leukotest or any other similar chamber, and attaching the patch onto the volunteer skin. Each patch contained the test material. The trial period was 6 weeks.

The test involved the application of the test article on the intrascapular region of the back or the arm of a group of 50 volunteer panelists. The panelists ranged from 18 to 65 years of age. These panelists were determined to be in good general health and free of any visible skin disease or anomaly in the area to be patched. Each panelist was requited to read, understand and sign an informed consent statement.

The test article (the composition of the invention prepared as described hereinabove) was tested as supplied or diluted. When dilution was necessary, for example 20 times, 2.0 grams of the material and 38.0 grams of D.I. water (total weight 40.0 grams) were stirred with magnetic rod or on a stirring plate until the solution was homogeneous. The final concentration of the product was 5.0% (w/w). 0.07-0.1 ml or gr. of the test material was applied in the test patch.

For wipe tests, the wipe fabric was impregnated with the test material (the composition of the invention).

Volunteers were visited at home. They read the information sheet and signed the consent form.

Study Schedule

Induction Phase: The patch was applied to its designated contact site and remained in place for 24 hours. At the end of this period the patch was removed and the site was examined for any dermal response. The panelists rested for 24 hours, after which the skin site was examined again. A patch was then applied to the same site as previously used. The second application was identical to the first and remained in place for 24 hours. This procedure was repeated on Mondays, Wednesdays and Fridays or Sundays, Tuesdays and Thursdays until a series of nine applications were made. The panelists examined the site for any dermal response and reported their observations prior to the next application. The same site was used throughout the study. Each application was put on and removed by the staff of the Institute. A quality control person monitored the adherence to study protocol.

Challenge Phase: Following the 9th application, a rest period of 2 weeks elapsed after which a challenge application was applied in the same manner and to the same site described above. The challenge application was removed after 24 hours and the site was examined and graded for signs of irritation or sensitization. A follow-up examination was conducted at 48 hours after the challenge application (24 hours after patch removal), as well as at 48 and 72 hours after removal.

Grading Scale

The treated skin area was graded according to the following scale:

0—No visible reaction

?—Doubtful reaction; faint, minimal erythema, no infiltration

1—Weak positive reaction: erythema, infiltration, discrete papules

2—Strong positive reaction: erythema, infiltration, papules, discrete vesicles

3—Extra positive reaction: intense erythema, infiltration, coalescing vesicles/bullous reaction IR—Irritation reaction: discrete erythema without infiltration/patchy follicular erythema/hemorrhagic and follicular pustules NT—Not tested Critical Events Definition: An adverse event is defined as any clinical or biological alteration to the initial condition of the subject (including intercurrent diseases), regardless of whether it was related to the tested product.

Adverse events: Serious adverse events included: hospitalization; life-threatening events; death; sequellae or partial or permanent invalidism Conditions for exit from the test were in accordance with the Helsinki/Tokyo/Venice declaration and Israeli law concerning the protection of subjects in biomedical research. Subjects had the right to leave the study at any time and for any reason. The investigator was authorized to terminate observation of the subject at any time if there was an intercurrent disease or an untoward event.

Inclusion Criteria

General criteria: subjects were aware of the test procedure and signed the consent form. They had to be cooperative, and fully cognizant of the necessity and the duration of the study controls and the importance of strict adherence to the protocol as determined by the ISR.

Specific criteria: gender: male or female; age: between 18 and 65 years.

Non-Inclusion Criteria

Population: pregnant or nursing women.

Associated pathology: cutaneous pathology on the treated zone; subjects suffering from serious or progressive diseases.

Previous or current treatment: subjects using a treatment (retinoids, anti-inflammatory substances such as steroids) and modifiers of the cutaneous hydration.

Personal hygiene and habits: unstable weight; excessive use of alcohol or tobacco.

Evaluation of Compliance

If a subject deviated from the protocol, and the deviation was minor, the technician responsible cautioned the subject about the importance of adhering to the prescribed protocol. If the subject persisted or the deviation was major, the subject was declared non-compliant and removed from the test for the reason of non-compliance.

Associated Treatment During the Study

No water was applied to the test site during application of the patch. No systemic or topical treatment likely to modify the skin was permissible. No use of dermopharmaceutical or cosmetic products, including cleansing products, was permissible on the zones being evaluated.

Application

The product was applied as an ointment by the Study Technician into the Finn Chamber/Hill Top Chamber/Leukotest or any other similar chamber, which was then applied on the intrascapular region of the back, or the arm.

The study was carried out on 50 volunteers, 12 male and 38 female subjects. Subjects ranged in age from 18 to 65 years: 20 subjects were 18 to 35, 13 subjects were 36-45, and 17 subjects were 46 to 65. All 50 subjects finished the study.

Results

The original patch sites exhibited no reactions during the Induction Phase, the Rest Period or the Challenge Phase. No other reactions were exhibited.

At the Challenge Phase (the 10th application), no reaction was observed in any of the volunteers.

Conclusion

In this RIPT Study performed according to the aforementioned Experimental Design, after repeated applications, the composition of the invention exhibited no disadvantageous reactions such as irritation or sensitization in the observed subjects during any stages of the test.

Example 4

Use of the Composition as Mosquito Repellent

Trial Goals

1. Evaluation of the effectiveness of the composition in preventing mosquitoes from landing on a skin area to which the composition is applied.
2. Evaluation of the effectiveness of the composition in preventing mosquitoes from biting the area to which the composition is applied
3. Evaluation of the composition's texture and the reaction of the treated skin area.

Materials and Methods

The evaluation was conducted at the Ministry of Health Laboratory, December 2007.

Two standard cages were used in this trail, each containing about 150 adults of the *Culex pipiens* mosquito species. The mosquitoes emerged from their pupae about 8 days before the trial began and were fed on sugar water, without any exposure to blood before the trial has started. The cage populations were both male and female mosquitoes in their natural ratios.

The composition, prepared as described above, formulated as a cream and stored in refrigeration, was applied thoroughly to the left hand up to the middle of the forearm of the subject. Application to this area required 4.3 g of the cream. Each hand was inserted into a different cage for different time periods in accordance with developments. Cages were changes every so often. The first exposure began abut five minutes after application of the composition. The temperature during the trail was 26-28° C.

Mosquitoes landing on the hands were observed carefully and mosquitoes were monitored to check any biting. No attempt was made to sexually identify (male/female) any mosquito landing on the hand.

Results

First exposure begun about 5 minutes after the cream was applied. Overall time exposure was 3 minutes. Number of mosquitoes landing on the hand is summarized in Table 2.

TABLE 2

Number of landing mosquitoes after first exposure

| Time from Beginning of Exposure (minutes) | Number of Mosquitoes Landing On The Hand | |
|---|---|---|
| | Control | Treated Area |
| 1 | 5 | 0 |
| 3 | 5 | 0 |

First mosquito bite was observed after about one minute of exposure

Second exposure began about 5 minutes after application of the test cream. Overall time exposure was 3 minutes. Number of mosquitoes landing on the hands is summarized in Table 3.

TABLE 3

Number of landing mosquitoes after second exposure

| Time from Beginning of Exposure (minutes) | Number of Mosquitoes landing on the Hand | |
|---|---|---|
| | Control | Treated Area |
| 1 | 5 | 0 |
| 3 | 9 | 0 |

First mosquito bite was observed after about one minute of exposure

At the end of the second exposure, the cages were changed. Third exposure has begun about 25 minutes after the cream composition was applied. Overall exposure time was 5 minutes. Number of mosquitoes landing on the hands is summarized in Table 4.

TABLE 4

Number of landing mosquitoes after third exposure

| Time from Beginning of Exposure (minutes) | Number of Mosquitoes landing on the Hand | |
|---|---|---|
| | Control | Treated Area |
| 0.6 | 1 | 0 |
| 1.0 | 9 | 0 |
| 1.5 | 14 | 0 |
| 2.0 | 17 | 0 |
| 3.0 | 20 | 1 |
| 3.5 | 25 | 2 |
| 5.0 | 21 | 2 |

Forth exposure began 60 minutes after application of the composition. Overall exposure time was 10 minutes. The number of mosquitoes landing on the hands and the number of bites are summarized in Table 5.

TABLE 5

Number of landing mosquitoes and mosquito bites after forth exposure

| Time from Beginning of Exposure (minutes) | Control | | Treated Area | |
|---|---|---|---|---|
| | Landing | Bites | Landing | Bites |
| 0.5 | 1 | 0 | 0 | 0 |
| 1.0 | 5 | 2 | 0 | 0 |
| 1.5 | 12 | 6 | 1 | 0 |
| 2.0* | | | 2 | 1 |
| 3.0 | | | 3 | 1 |
| 4.5 | | | 2 | 2 |
| 5.5 | | | 3 | 2 |
| 6.0 | | | 3 | 2 |
| 6.5 | | | 4 | 1 |
| 7.0 | | | 6 | 2 |
| 8.0 | | | 2 | 2 |
| 8.5 | | | 4 | 2 |
| 10.0 | | | 2 | 1 |

*After landing and bites were observed on the untreated area, 2.0 minutes from the beginning of the exposure, the untreated hand was removed from the cage to maintain availability of hungry female mosquitoes.

Fifth exposure began 120 minutes after application of the composition. Overall exposure time was 5 minutes. The number of mosquitoes landing on the hands and the number of bites are summarized in Table 6. After 4 minutes of exposure the untreated hand was removed from the cage to maintain sufficient number of available hungry female mosquitoes.

TABLE 6

Number of landing mosquitoes and mosquito bites after fifth exposure

| Time from Beginning of Exposure (minutes) | Control | | Treated Area | |
|---|---|---|---|---|
| | Landing | Bites | Landing | Bites |
| 1.0 | 1 | 0 | 1 | 0 |
| 1.5 | 5 | 3 | 2 | 0 |
| 2.0 | 11 | 5 | 2 | 0 |
| 2.5 | 18 | 6 | 2 | 0 |
| 4.0* | | | 2 | 0 |
| 5.0 | | | 0 | 0 |

After completion of the fifth exposure, the cages were changed. Sixth exposure began 180 minutes after applying the cream. Overall exposure time was 5 minutes. The number of mosquitoes landing on the hands and the number of bites are summarized in Table 7. After 3 minutes of exposure the untreated hand was removed from the cage to maintain sufficient number of available hungry female mosquitoes.

TABLE 7

Number of landing mosquitoes and mosquito bites after sixth exposure

| Time from Beginning of Exposure (minutes) | Control | | Treated Area | |
|---|---|---|---|---|
| | Landing | Bites | Landing | Bites |
| 0.5 | 1 | 0 | 0 | 0 |
| 1.0 | 3 | 0 | 0 | 0 |
| 1.5 | 8 | 2 | 0 | 0 |
| 2.0 | 15 | 7 | 0 | 0 |
| 3.0* | 8 | | 0 | 0 |
| 3.5 | | | 1 | 0 |
| 4.0 | | | 3 | 0 |
| 4.5 | | | 4 | 1 |
| 5.0 | | | 7 | 2 |

Conclusions

The trail was conducted as an initial evaluation of the composition efficacy in preventing biting by female mosquitoes. The experimental setup was found to be satisfying as the female mosquitoes were hungry and the host hand was found to be sensitive to the female mosquitoes. Throughout the entire trial, the untreated hand area attracted females that were landing and biting.

During the first two exposures, no landings were observed on the treated hand. The first landing was observed during the third exposure, about half an hour after application was completed. During the first three exposures, for about half hour after the composition was applied, no bites were observed on the treated hand area. Changing cages between the second and the third exposure had no significant effect.

During the exposure beginning one hour after the composition was applied, mosquitoes landing on the treated area were observed, as well as bites.

During the exposure beginning two hours after the composition was applied, only few mosquitoes landing on the treated area were observed, with no subsequent biting. Changing cages between the fifth and the sixth exposure had no significant effect.

In summary, the composition of the invention is efficient in preventing mosquitoes from landing on and biting human skin area. Prolonging the duration of protection may be achieved by using more concentrated formulations.

Example 5

Compositions for Preserving Fresh Produce and their Use

Composition for Application to Fresh Produce

| Compound | Concentration (%) |
|---|---|
| Stage 1 | |
| Oleic acid | 0.1-4 |
| Lauric acid | 0.1-6 |
| Myristic acid | 0.1-3 |
| Stearic acid | 0.1-2 |
| Total fatty acids | 1-4 |
| Carnauba wax | 7-20 |
| KOH-solid | 0.08-3 |
| Glycerin | 0.8-6 |
| Ammonia | 0.1-3 |
| Anti-foam | 0.001-1 |
| Demineralized water | 52-91.2 |
| Stage 2 | |
| Stage 1 | 64-98 |
| Demineralized water | 1-30 |
| L-lysine | 1-6 | pH of the composition: 7.0-9.5

Preparation Procedure

In a reactor, melted wax and fatty acids were melted at 110° C., and then a solution of KOH in glycerin was added. The temperature of the mixture was raised to 120° C., and this temperature was maintained for about 10-30 min. Hot water (about 99° C.) was then added slowly (during a period of about 10-150 min) to the bottom of the reactor, while the temperature is kept at 90-120° C. At this stage, ammonium hydroxide ($NH_4OH$) was also added to reach a mixture pH of above 10. After all water was added and stirred, the temperature was lowered to below 30° C. as fast as possible. At the end of this stage, a brown (due to the presence of $NH_4OH$) transparent emulsion was obtained. The ammonium hydroxide should be removed to avoid the unpleasant odor associated with this compound. Therefore, the mixture temperature was again elevated above 100° C. and ammonium was removed using Reflux and Scrubber until the pH of the emulsion was below 10. At the last stage, the emulsion was cooled again to a temperature below 30° C. The obtained emulsion was then mixed with demineralized water (1%-30% w/w in respect to the total weight of the composition) and lysine (1%-6% w/w).

The experiments described hereinbelow are preliminary tests performed at a small scale with 10-100 units (fruit). The composition of the invention prepared as described in this example (designated hereinafter "fruit composition") was applied to the fruit as indicated. When possible, comparison with known coating material including carnauba wax was made.

Fruit of Green Lime (*Citrus aurantifolia*) from Thailand

Lime fruit harvested in the mountains of Thailand change their skin color from green to brown and become dry about 24 h after harvest, even when the fruit are coated with commercially available fruit-coating wax and/or stored at cooling system.

Figure 2:
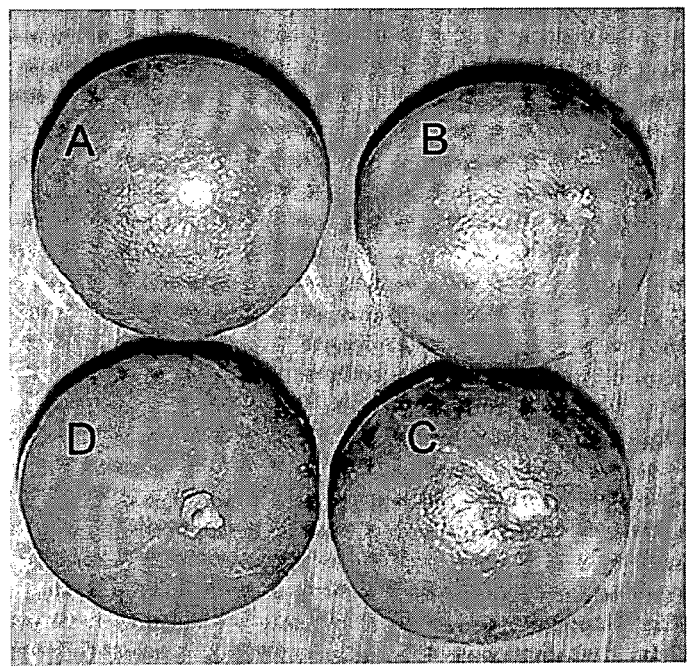
FIG. 2 shows lime fruit coated (fruit A-C) and uncoated (fruit D) with the fruit composition of the invention, stored at 25-28° C. for 30 days.

Lime fruit were immersed in or sprayed with the fruit composition of the invention 8-12 hours after harvest. Fruit were then dried at room temp (35° C., humidity 85%-95%), and stored under air-conditioning system (25-28° C.) for 30 Days. Control fruit (no treatment applied) were also stored under the same conditions. The air-conditioning system was turned off during the nights and the weekends. After 30 days, fruit were examined for their appearance. All fruit coated with the fruit composition of the invention were green, and looked shiny and fresh. In contrast, control fruit were brown and dry (FIG. 2).

Avocado (*Persea Americana*) Fruit

The experiment aimed at evaluating the effect of the fruit composition of the invention on the storability of non-ripe avocado fruit treated close to harvest and on half-ripe fruit showing initial signs of decay.

Medium to large size fruits (about 150-250 g) of the "Atinger" cultivar were obtained from a packinghouse in Maanit, Israel, transported to Lederman Laboratory (Hod Hasharon, Israel) on the day of harvest, and kept at 25° C. until the next morning, when they were sorted to eliminate defected fruit and divided to the following sample groups:

Sample 1—18 non-ripe fruit coated with the fruit composition of the invention and stored outdoors at 25-28° C. for 30 days.

Sample 2—10 non-ripe uncoated fruit serving as a control stored outdoors at 25-28° C. for 30 days.

Sample 3—18 half ripe "Atinger" fruit showing initial signs of decay on the top of avocado, coated with the fruit composition of the invention and stored outdoors at 25-28° C. for 30 days.

Fruit of all three sample groups were examined for visible changes each week and evaluated for change in external color and general decay. Individual fruit weight was recorded every week until the fruit were discarded.

Non-ripe fruit coated with the fruit composition of the invention showed no sign of decay at the end of the experiment (after 30 days). Fruit skin was green and the inside clean lemon-yellow.

Half ripe fruit coated with the fruit composition of the invention preserved the initial decay signs observed at the beginning of the assay for additional 15-18 days, after which further decay signs, including softening and brown spots were observed.

Control uncoated avocado fruit showed decay signs after 10 days, including softening, shriveling and blackening, such that the fruit were not acceptable for human consumption.

Figure 3:
FIG. 3 shows non-ripe avocado (*Persea Americana*) fruit coated (left hand side) and non-coated (right hand side) with the fruit composition of the invention and stored at 25-28° C. For 30 days.

In summary, the fruit composition of the present invention significantly preserved the storability of the avocado fruit (FIG. 3).

Green Sweetie Fruit (*Citrus paradisi*×*Citrus maxima*)

In the citrus fruit of "green sweetie", it is important to preserve the green color and firmness of the fruit peeling.

150 units of green and clean sweetie fruit were harvested, washed and dried. Yellow spots present on the peel at the time of harvest were marked (by paint), and each fruit was weighed. The fruit were divided to the following groups:

Control—uncoated fruit (30 units) packed in a single carton box and stored in refrigerated container at 7-10° C.

Positive control—fruit coated with commercially available carnauba wax product (60 units) packed in a single carton box and stored in refrigerated container at 7-10° C.

Test—fruit coated with the fruit composition of the invention (60 units) packed in a single carton box and stored in refrigerated container at 7-10° C.

All three groups were stored for 30 days, with yellow spots, weight loss and general signs of decay examined each week. The results are summarized in Table 8 hereinbelow.

TABLE 8

Comparative experiment with different coatings

|  | Control | Positive Control | Test |
|---|---|---|---|
| Average weight at starting point | 380 g | 377 g | 344 g |
| Average weight loss | 40 g (10.3%) | 20.8 g (5.51%) | 21.8 (6.4%) |
| Yellow peeling | 30 unite (100%) | 9 units (15%) | 0 units (0%) |
| Green peeling | 0 units (0%) | 20 units (33%) | 52 units (87%) |
| Decay signs and presence of fungi | 30 units (100%) | 15% of the units | None of the units |
| Physical conditions | All units are unsuitable for eating | All units suitable for eating, firm peeling | All units suitable for eating, firm green peeling |

In summary, the fruit composition of the present invention was found to be highly effective in preserving all desired parameters of fresh sweetie fruit. The composition was superior over commercially available coating composition in preserving the fruit green color and preventing decay signs on the fruit.

Pomegranate Fruit (*Punica granatum*)

Pomegranate fruit are highly susceptible to storage conditions. The study presented below examined the effect of the fruit composition of the invention on the storability of pomegranate fruit of the "Wonderful" cultivar under storage conditions of 7° C. and of 25-28° C., 65-90% humidity, for 30 days.

Medium/large size fruits (about 290-670 g per unit), 50 units of the "Wonderful" cultivar were obtained from a packing house in Maanit, Israel and transported to Lederman Laboratory (Hod Hasharon, Israel) on the day of harvest.

Color of fruit at picking was red or yellow. All fruits were kept at 7° C. until the next morning, when they were sorted to eliminate defects, and then divided into comparable sample groups as follows:

Sample 1—20 Fruit coated with the fruit composition of the invention

Sample 2—20 uncoated fruit (control).

Each sample was divided to two groups—one group stored at 7° C. and one group stored at 25-28° C., 65-90% humidity. All groups were stored for 30 days. Fruit were examined for external appearance and weight at the starting point of the study ($T_0$) and at the end of the study (after 30 days). At the end of the study fruit were also examined for internal parameters including juice color, Brix, pH, grain weight and internal signs of decay.

For measuring juice parameters, the fruit arils were separated from other tissues and their juice was extracted using a hand-operated citrus squeezer. The juice was filtered through cheesecloth, and then color, Brix and pH were measured. Brix was measured with a temperature-compensated refract meter; pH with a pH-meter. The results are summarized in Tables 9 and 10 hereinbelow

TABLE 9

Control and coated pomegranate fruit stored at 7° C.

| Parameter | Test- coated fruit stored at 7° C. | Control (no coating) stored at 7° C. |
|---|---|---|
| Average weight at starting point | 670 g | 622 g |
| Average weight loss | 107 g (15.9%) | 89 (14.3%) |
| Skin color at $T_0$ | Red-pink | Red-pink |
| Skin color after 30 days of storage | Strong red-pink | Strong red |
| External decay signs and presence of fungi | None of the units | 16 units (80%) |
| Physical conditions | All units are suitable for eating, hard skin | All units are dry and shriveled |
| Average weight of grains (from 20 units) | 310 g | 316 g |
| Average weight of juice | 230 | 200 |
| Juice Brix | 13.5 | 15.5 |
| Juice pH | 4.5 | 5.25 |
| Juice taste | Sweet, no aftertaste | Very sweet, fermentation aftertaste |
| Internal decay signs and presence of fungi | None | Signs of fermentation |

TABLE 10

Control and coated pomegranate fruit stored at 25° C.

| | Test- coated fruit stored at 25° C. | Control (no coating) stored at 25° C. |
|---|---|---|
| Average weight at starting point | 350 g | 300 g |
| Average weight loss | 42 g (15.9%) | 87 (29%) |
| Skin color at $T_0$ | Green, Yellow | Green |
| Skin color after 30 days of storage | Green, Yellow | Vary (green, red, yellow, pink) |
| External decay signs and presence of fungi | None of the units | None of the units |
| Physical conditions | All units are suitable for eating, hard skin | All units are dry and shriveled |
| Internal decay signs and presence of fungi | None | Signs of decay |

As is apparent from Table 9 and 10 pomegranate fruit coated with the fruit composition of the invention preserved the skin color and fruit shape compared to the non-coated fruit that were dry and shriveled at the end of the study when stored at 7° C. as well as at 25-28° C. No significant difference was found in fruit weight at the end of the study when the control and coated fruity were stored at 7° C.; however, the weight loss of coated fruit stored at 25-28° C. was lower compared to uncoated fruit.

The foregoing description of the specific embodiments will so fully reveal the general nature of the invention that others can, by applying current knowledge, readily modify and/or adapt for various applications such specific embodiments without undue experimentation and without departing from the generic concept, and, therefore, such adaptations and modifications should and are intended to be comprehended within the meaning and range of equivalents of the disclosed embodiments. It is to be understood that the phraseology or terminology employed herein is for the purpose of description and not of limitation. The means, materials, and steps for carrying out various disclosed functions may take a variety of alternative forms without departing from the invention.

The invention claimed is:

1. A composition for administration to a mammalian skin surface comprising an aqueous phase, carnauba wax, at least one fatty acid comprising a chain having from 8 to 18 carbon atoms, lysine or a salt thereof, and a base comprising potassium hydroxide, wherein the carnauba wax concentration is at least 5% by weight with respect to the total weight of the composition, the ratio of the at least one fatty acid to carnauba wax is at least 1:3 (w/w) and the ratio of the combined total amount of said carnauba wax and at least one fatty acid to lysine is at least 4:1 (w/w).

2. The composition of claim 1, wherein the carnauba wax concentration is from 7% to 40% by weight with respect to the total weight of the composition.

3. The composition of claim 1, wherein the fatty acid is selected from the group consisting of lauric acid, myristic acid, stearic acid, palmitic acid, arachidic acid, behenic acid, palmitoleic acid, oleic acid, linoleic acid and combinations thereof.

4. The composition of claim 3, comprising a combination of lauric acid, myristic acid, oleic acid and stearic acid.

5. The composition of claim 1, wherein the at least one fatty acid concentration is from 1.6 to 30% by weight with respect to the total weight of the composition.

6. The composition of claim 5, wherein the at least one fatty acid concentration is from 1.6% to 10% by weight with respect to the total weight of the composition.

7. The composition of claim 1, wherein the lysine concentration is from 1.6% to 15% by weight with respect to the total weight of the composition.

8. The composition of claim 1, wherein the carnauba wax has a concentration in the range of 7%-30%, wherein the at least one fatty acid has a total combined concentration in the range of 1%-6%, and wherein the at least one fatty acid comprises a combination of: oleic acid in the range of 0%-4%, lauric acid in the range of 0%-6%, stearic acid in the range of 0%-2%, and myristic acid in the range of 0%-3%, and wherein the lysine has a concentration in the range of 1%-6%, all by weight with respect to the total weight of the composition.

9. The composition of claim 1, further comprising at least one surfactant selected from the group consisting of diglycerin, glycerin, glycerol, glycerol polymers, glycol, glycol stearate, glycol stearate SE, propylene glycol, avocado (Persea gratissima) oil, honey, glyceryl distearate, glyceryl hydroxystearate, glyceryl laurate, glyceryl linoleate, glyceryl myristate, glyceryl oleate, glyceryl stearate, paraffin, propylene glycol dipelargonate, propylene glycol laurate, propylene glycol stearate, propylene glycol stearate SE and stearoxy.

10. The composition of claim 1, further comprising at least one complex sugar selected from the group consisting of fructose, glucose, sucrose, sucrose fatty acid ester, sucrose acetate isobutyrate (SAIB), and sorbitol.

11. The composition of claim 1, further comprising at least one preservative.

12. The composition of claim 1, further comprising at least one viscosity agent selected from the group consisting of sodium polyacrylate and ethylhexyl stearate.

13. The composition of claim 1, further comprising hyaluronic acid.

14. The composition of claim 1, being a cosmetic or pharmaceutical composition further comprising a cosmetically or pharmaceutically acceptable diluent or carrier, said composition having a viscosity of from 1,000 to 100,000 cps at a temperature of about 20° C.

15. The composition of claim 14 having a pH in the range of 6.5-8.5.

16. A method of treating skin irritation, skin itching, pruritus, sore skin, redness, burns and wounds comprising topically applying to the skin of a subject in need thereof an effective amount of the composition of claim 1.

17. The method of claim 16 wherein the sore skin or wound results from diabetes.

18. A method of treating herpes virus sores comprising topically applying to the skin of a subject in need thereof a therapeutically effective amount of the composition of claim 1.

19. A method of treating irritation resulting from insect bites comprising topically applying to the skin of a subject in need thereof an effective amount of the composition of claim 1.

20. The method of claim 19, wherein the insect is mosquito.

21. A method of repelling mosquitoes from a mammalian skin comprising topically applying to the skin an effective amount of the composition of claim 1.

* * * * *